(12) United States Patent
Taylor et al.

(10) Patent No.: US 9,541,524 B2
(45) Date of Patent: Jan. 10, 2017

(54) SYNCHRONIZED ION MODIFICATION

(71) Applicant: Smiths Detection—Watford Ltd., Herts (GB)

(72) Inventors: Stephen J. Taylor, Buckinghamshire (GB); Jonathan R. Atkinson, Herts (GB)

(73) Assignee: Smiths Detection-Watford Limited, Hemel Hempstead (GB)

(*) Notice: Subject to any disclaimer, the term of this patent is extended or adjusted under 35 U.S.C. 154(b) by 0 days.

(21) Appl. No.: 14/370,838

(22) PCT Filed: Feb. 15, 2013

(86) PCT No.: PCT/IB2013/000617
§ 371 (c)(1),
(2) Date: Jul. 7, 2014

(87) PCT Pub. No.: WO2013/121287
PCT Pub. Date: Aug. 22, 2013

(65) Prior Publication Data
US 2015/0069229 A1    Mar. 12, 2015

Related U.S. Application Data

(60) Provisional application No. 61/599,499, filed on Feb. 16, 2012.

(51) Int. Cl.
*G01N 27/62* (2006.01)
(52) U.S. Cl.
CPC ................. *G01N 27/622* (2013.01)
(58) Field of Classification Search
USPC ........ 250/282, 286, 287, 288, 292, 283, 281
See application file for complete search history.

(56) References Cited

U.S. PATENT DOCUMENTS

2006/0071159 A1* 4/2006 Hashimoto .......... G01N 27/622
  250/287
2009/0039248 A1* 2/2009 Atkinson ............ H01J 49/0045
  250/286
(Continued)

FOREIGN PATENT DOCUMENTS

CN       1758057 A    4/2006
CN      101641593    2/2010
(Continued)

OTHER PUBLICATIONS

Nagato, Kenkichi, "Development of an Ion Mobility/Mass Spectrometer", J. Aerosol Res., Jpn., 15 (2), pp. 110-115, 2000.
(Continued)

*Primary Examiner* — Phillip A Johnston
*Assistant Examiner* — Hsien Tsai
(74) *Attorney, Agent, or Firm* — Advent, LLP

(57) ABSTRACT

Synchronized ion modification systems and techniques are described. An ion modifier can be used to modify a portion of ions that enter a drift chamber via a gate that controls entry of the ions to the drift chamber. A controller that is communicatively coupled to the ion modifier is configured to control the ion modifier to select a portion of the ion to be modified. In embodiments, the controller selects the portion based on a detector's previous response to other ions that are formed from a sample from which the ions were formed. The other ions, for example, correspond to ions that are associated with a peak in previous operation of a spectrometer.

29 Claims, 5 Drawing Sheets

(56) References Cited

U.S. PATENT DOCUMENTS

2009/0189064 A1* 7/2009 Miller ................ G01N 27/624
　　　　　　　　　　　　　　　　　　　　　　250/282
2010/0230588 A1* 9/2010 Atkinson ................ H01J 49/40
　　　　　　　　　　　　　　　　　　　　　　250/283

FOREIGN PATENT DOCUMENTS

| CN | 201589766 U | 9/2010 |
| DE | 19727122 C2 | 5/1999 |
| EP | 1646068 | 4/2006 |
| EP | 2122340 | 11/2009 |
| JP | 2008527396 A | 7/2008 |
| JP | 2008538849 A | 11/2008 |
| WO | 2006114580 | 11/2006 |
| WO | 2007080376 | 7/2007 |
| WO | 2007086831 A2 | 8/2007 |

OTHER PUBLICATIONS

Japanese Office Action for Japanese Appln. No. 2014-557131.
Mexican Office Action for Mexican Appln. No. 2014-557131, dispatched Sep. 1, 2015.
Chinese Office Action for Chinese Appln. No. 201380000917.1, dated Nov. 16, 2015.

* cited by examiner

SYNCHRONIZED ION MODIFICATION

BACKGROUND

Ion mobility spectrometers (IMS) can identify material from a sample of interest by ionizing the material (e.g., molecules, atoms, and so forth) and measuring the time it takes the resulting ions to reach a detector. The ion's time of flight is associated with its ion mobility that relates to the mass and geometry of the molecule that was ionized. The detector's output can be visually represented as a plasmagram of peak height versus drift time.

At times, it can be difficult to identify some ions represented in a plasmagram. Contaminants, operating conditions, ions with similar geometries and masses and so on can impact an IMS's ability to detect and identify ions. For example, a sample that is contaminated may have a misshapen or a comparatively small peak height.

SUMMARY

Synchronized ion modification systems and techniques are described. An ion modifier can be used to modify a portion of ions that enter a drift chamber via a gate that controls entry of the ions to the drift chamber. A controller that is communicatively coupled to the ion modifier is configured to control the ion modifier to select a portion of the ion to be modified. In embodiments, the controller selects the portion based on a detector's previous response to other ions that are formed from a sample from which the ions were formed. The other ions, for example, correspond to ions that are associated with a peak in previous operation of a spectrometer.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION

Figure 1:
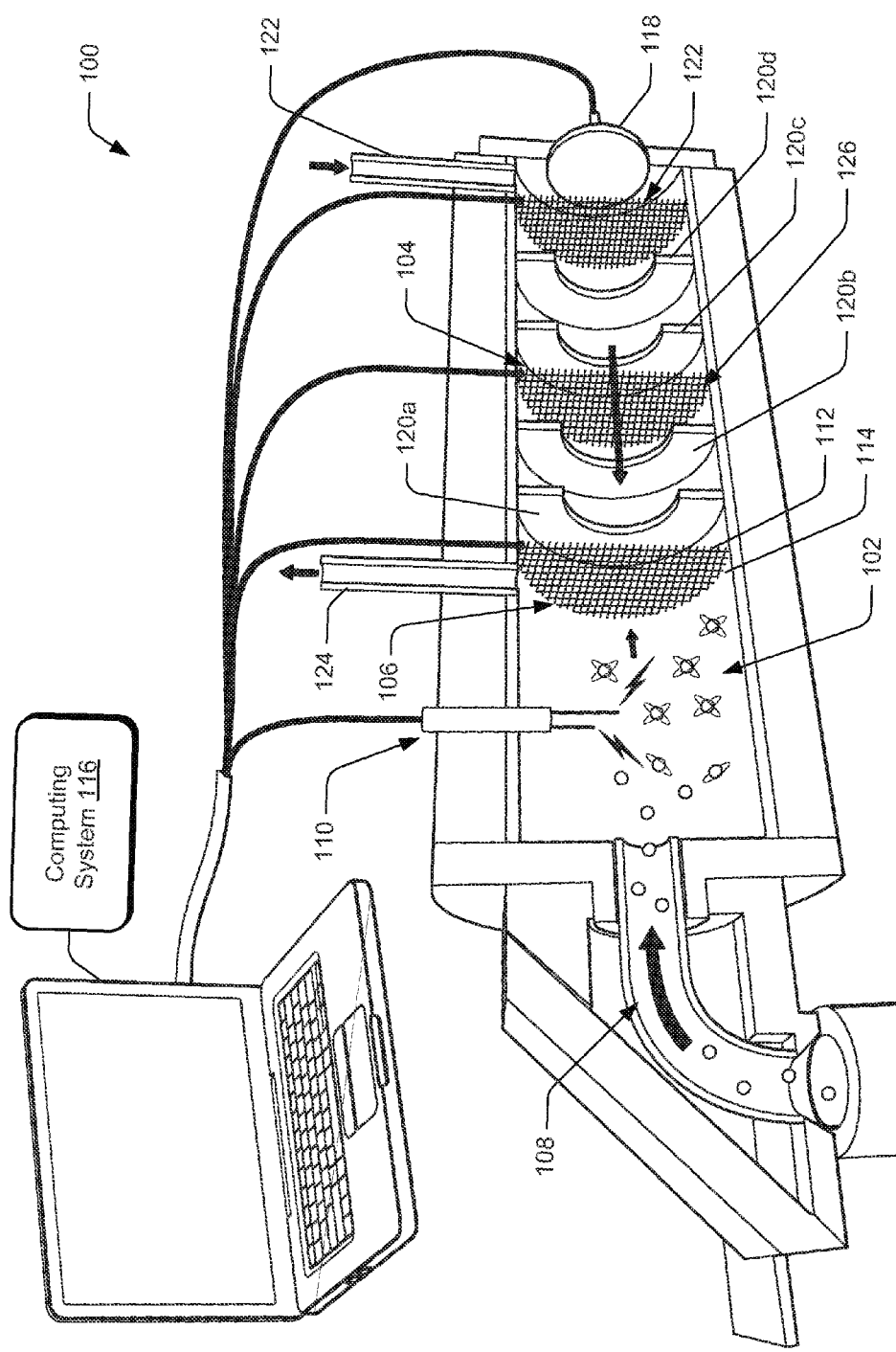
FIG. 1 is an illustration of a spectrometer configured to implement an ion modifier in accordance with the present disclosure.

FIG. 1 is an illustration of a spectrometer, such as an ion mobility spectrometer (IMS) 100. Although IMSs are described herein, it is to be apparent that a variety of different types of spectrometer can benefit from the structures, techniques and approaches of the present disclosure. It is the intention of this disclosure to encompass and include such changes.

The IMS 100, as illustrated, includes an ionization chamber 102 that is separated from a drift chamber 104 via a gate 106. The gate 106 can control passage of ions from the ionization chamber 102 into the drift chamber 104. For example, the gate 106 is configured to have a charge applied/dropped to control when and what ions can enter the drift chamber 104. The gate 106 can comprise any suitable gate including, but not limited to, a Bradbury-Nielsen gate and a Tyndall Powell gate.

The IMS 100, as illustrated, includes an inlet 108 for introducing material from a sample of interest to the ionization chamber 102. The inlet 108 can employ variety of sample introduction approaches. Although a flow of air (e.g., an airflow) can be used, the IMS 100 can use a variety of other fluids and/or gases to draw material into the inlet 108. Approaches for drawing the material through the inlet include the use of fans, pressurized gases, a vacuum created by a drift gas flowing through the drift chamber, and so forth. The IMS 100 can operate substantially at ambient pressure, although a stream of air or other fluid is used to introduce the material into the ionization chamber.

In embodiments, the IMS 100 includes other components to aid introduction of material from the sample. For example, a desorber, such as a heater, is included to cause at least a portion of the sample to vaporize and/or enter its gas phase so it can be drawn into the inlet 108. The IMS 100 can include a pre-concentrator to concentrate or cause a bolus of material to enter the ionization chamber 102.

The IMS 100 can include a variety of components to promote identification of the molecule of interest. For example, the IMS 100 includes one or more cells to contain calibrant and/or dopant. The cells can provide dopant to one or more of the inlet, the ionization chamber or the drift chamber. Dopant is combined with the molecule and ionized to form an ion that is more effectively detected than an ion that corresponds to the molecule alone. The IMS can be configured to provide dopant to different locations, at different times during operation of the IMS. The IMS can coordinate dopant delivery with operation of other components in the IMS.

An ionization source 110, as illustrated, is disposed in the ionization chamber 102. Example ionization sources include, but are not limited to, radioactive and electrical ionization sources, such as, a corona discharge source, photoionization source, electrospray source, matrix assisted laser desorption ionization (MALDI) source, a nickel 63 source ($Ni^{63}$), and so forth.

In embodiments, the IMS 100 operates in positive mode, negative mode, switches between positive and negative mode, and so forth. In positive mode, for example, the ionization source 110 generates positive ions from molecules included in the material from the sample of interest. In negative mode, the ionization source 110 can generate negative ions. Whether the IMS 100 operates in positive mode, negative mode, or switches between positive and negative modes can depend on implementation preferences, a predicted sample type (e.g., explosive, narcotic, toxic industrial chemicals) and so forth. An electrical ionization source and/or the ionization chamber's walls can switch between positive and negative modes at approximately twenty (20) milliseconds, ten (10) milliseconds (ms), or less intervals—although a variety of timing scenarios are contemplated.

The ionization source's operating configuration can vary based on operating preferences. Example configurations include, but are not limited to, one or more of voltage and current (for electrical sources), inlet flow rate or a drift gas flow rate. Other configurations include, an expected amount of the sample to be ionized, a voltage difference between the ionization source and one or more walls forming the ionization chamber 102, or the ionization source. For example, the IMS 100 pulses the ionization source 110 periodically, based on sample introduction, gate opening, upon the occurrence of an event, and so on.

The ionization source 110 can generate a variety of ions with different mass to charge ratios. For example, the ionization source 110 generates an ion comprising a molecule with a positive or negative charge. The ionization source 110 can ionize molecules from sample of interest in multiple steps. For example, the ionization source 110 generates a corona that ionizes gases in the ionization chamber that subsequently used to ionize the molecule of interest. Example gases include nitrogen, water vapor, gases included in air and other gases in the ionization chamber.

In embodiments, wall(s) forming the ionization chamber are electrically conductive so a charge difference can exist between the ionization source and the walls, when the IMS includes an electrical ionization source. In operation, the charge difference may cause ions from a corona to be drawn away from the source to ionize material from the sample of interest. While the ions can be drawn away from the ionization source, the ions are prevented from entering the drift region. Ions that pass toward the gate while it is closed may be neutralized as the ions contact the gate.

In embodiments, the gate 106 controls entrance of the ions to drift chamber 104. For example, the gate 106 comprises a mesh of wires to which an electrical charge is applied/removed. In embodiments, the mesh of wires that forms the gate 106 includes a fixed grid 112 and a moving grid 114. The gate 106 can control ions entering the drift chamber by dropping a charge on the moving grid to "open" the gate.

For example, a Bradbury Neilson gate can be constructed from two (approximately coplanar) sets of interdigitated wires. When the gate is to be closed, one of the sets of wires is set to be at a different potential than the other, e.g., a difference of about 50V. Ions therefore experience a strong electric field at 90 degrees to their normal direction of travel, and hit the wires and are neutralized. When the gate is opened, the two sets of wires are set to be at the same potential—the ions then only experience the normal IMS field which carries them into the drift region.

A controller, such as a computer controller 116, can be used to control opening/closing of the gate. In examples, the controller controls what voltage is applied to the gate (e.g., the moving and fixed grids 112, 114), how the voltage is applied and so on. Operation of the gate can be controlled to occur periodically, upon the occurrence of an event, and so forth. The controller can adjust how long the gate is open or closed based on occurrence of an event (e.g., corona discharge), periodically, and so forth. For example, the controller can switch the charge applied to the gate based on the ionization source's mode.

As illustrated in FIG. 1, the drift chamber includes a detector 118 that is disposed generally opposite the gate 106. The drift chamber, in embodiments, is used to separate ions admitted to the drift chamber based on the individual ions' ion mobility. Ion mobility is determined by the charge on the ion, the ion's mass, geometry, and so forth. In this manner, the IMS 100 can separate ions based on their time-of-flight. The drift chamber, in embodiments, has a substantially uniform electrical field that extends from the gate 106 to the detector 118.

The detector 118 can be a charged plate (e.g., Faraday plate) that detects ions based on their charge as they contact the plate. The computer controller 116 can identify the molecules from their corresponding ions. The IMS may differentiate between ions based on an ion's ion mobility.

A series of electrodes 120a-d (e.g., focusing rings) and/or a guard grid 122 are included in the drift chamber 104 in embodiments. The focusing rings can focus and/or direct the ions toward the detector 118. The guard grid 122 screens the detector electrode from the oncoming ions—without the screen grid present, the detector would register the presence of an ion significantly prior to it actually reaching the detector electrode. In embodiments, the electrodes 120a-d are ring shaped and disposed along the length of the drift chamber 104. The focusing rings, during operation, can form an electric field in the drift chamber to aid separation of the ions and/or focus ions towards the detector. The drift chamber, including the focusing rings, can apply a substantially uniform field in the drift chamber. For example, the focusing rings draw and/or aid directing ions toward the detector 118.

In embodiments, the IMS causes a drift gas to flow (flows a drift gas) in a direction generally opposite the ion's path of travel to the detector. For example, the drift gas flows from adjacent the detector 118 toward the gate 106. As illustrated, a drift gas inlet 122 and drift gas outlet 124 are used to flow the drift gas through the drift chamber. Example drift gases include, but are not limited to, nitrogen, helium, air, air that is re-circulated (e.g., air that is cleaned and/or dried) and so forth.

In embodiments, an ion modifier 126 is included in the drift chamber. The ion modifier can comprise one or more electrodes, disposed in the drift chamber between the gate and the detector. The ion modifier can include two or more electrodes that are spaced apart from one another along the drift chamber's length. For example, the ion modifier comprises a mesh of wires.

The ion modifier 126 can modify ions, such as through use of a radio frequency (RF), as they drift toward the detector 118. The ion modifier 126 can selectively modify a portion of the ions that entered the drift chamber. For example, the ion modifier modifies ions that have substantially similar ion mobilities, e.g., correspond to ions associated with a common peak, an overlapping, or an adjacent peak during previous operation of the IMS. Thus, the ions admitted to the drift chamber can separate (e.g., based on their respective ion mobilities) between the gate 106 and the ion modifier 126 so the ion modifier can modify a portion of the ions (e.g., selected ions) while not modifying others.

Modifying ions can include, but is not limited to, fragmenting the ions, changing the mass to charge ratio of the ions, and so forth. In examples, the ion modifier is configured to prevent other ions that are not included in the portion of ions from passing to the detector. While the ion modifier can provide a direct current field, in other embodiments, the ion modifier uses an alternating current field and/or switches polarity on occurrence of an event. The ion modifier can neutralize other ions while permitting selected ions to pass towards the detector. In embodiments, the ion modifier temporarily prevents ions from passing to the detector, such as by pulsing a charge to neutralize selected other ions. For example, the selected group of other ions can be chosen based on the ions' time of flight and so on. In embodiments, the controller and/or the ion modifier can be configured to cause some of the other ions to be neutralized while not neutralizing different ions in the other ions. The ion modifier can, for example, neutralize other ions that are adjacent to a peak of interest, that would interfere with ions of interest, ions that would overwhelm the detector, and so on while not neutralizing other ions.

In this manner, the ion modifier can allow ions to pass through it, or it can prevent ions from passing through it. Operation of the ion modifier 126 can be synchronized with operation of the gate 106. For example, the ion modifier can modify at a predetermined time after the gate opens. The ion modifier can modify ions that correspond to ions in a peak in a previous run to aid in identification of molecules from the sample.

In embodiments, the ion modifier varies what energy is applied to the ions. The ion modifier 126 can increase (ramp-up) the energy applied to the ions, switch polarity during operation, and so forth. For example, the ion modifier may operate in positive mode and then switch polarity to negative mode.

The ion modifier 126 can be positioned to permit separation of the ions entering the drift chamber and/or separation of ions that result from modifying a selected portion of the ions. For example, the ion modifier 126 is positioned so fragments, which result from the modifying, separate between the ion modifier and the detector based on their respective ion mobilities.

The ion modifier's position in the drift chamber can vary based on design preference, expected material, expected material type, ions/modified ions, fragments of ions, operating conditions, and so forth. The ion modifier, for example, is disposed midway or approximately at the midpoint of the drift chamber to permit separation of the ions entering via the gate, as well as the modified ions that result from operation of the gate. In some instances, the ion modifier is disposed adjacent the gate but at a sufficient distance to permit separation of the modified ions between the ion modifier and detector. In other instances, the ion modifier is placed closer to the detector than the drift chamber's midpoint to permit separation of the ions entering the drift chamber while permitting sufficient separation of the fragments that result from modifying the ions.

The ion modifier can selectively modify some of the ions while not modifying other ions and/or modifying ions differently, e.g., applying a (comparatively) higher charge on some of the ions while applying a lower or different charge on other ions. In embodiments, the ion modifier prevents non-selected ions, that would interfere with detection of selected ions, from reaching the detector while modifying selected ions. Thus, ions associated with a peak adjacent a peak of interest in a previous run may be neutralized while ions corresponding to the peak of interest are fragmented to aid identification of the material, e.g., molecules, from the sample.

A controller, such as the computing system 116, can be included the spectrometer to control operation of the ion modifier 126. The computing system 116, as illustrated, is communicatively coupled to the ion modifier to control its operation. The computing system 116 can perform other functions, such as analyzing detector output (e.g., identification of the sample of interest based on the ions), controlling operation of the gate (opening/closing), controlling operation of the IMS, and so forth, although the controller can be dedicated to controlling the ion modifier.

The computing system 116 can control operation of the ion modifier based on a result of previous operation of the spectrometer. For example, a control determines when and/or how the ion modifier operates, based on detector output during previous analysis of material from the sample of interest. In this manner, the controller selects which portion of the ions are to be modified based on the detector's previous response. The controller 128 can cause the ion modifier to operate based on ambiguous identification. Ambiguous identification can include, but is not limited to, partial identification; non-identification, non-detection, and so forth. For example, the controller may turn-on the ion modifier in a subsequent run to aid in differentiating ions from adjacent peaks during previous operation of the IMS. In embodiments, the controller 128 varies operation of other components in the IMS with operation of the ion modifier. For example, the controller controls how the gate 106 opens/closes in a subsequent run to coordinate operation of the ion modifier.

In embodiments, the IMS can time arrival of at least some ions at the detector with one or more of operation of the gate or ion modifier. In this manner, ions (such as fragments) that result from modifying ions that passed the ion modifier at approximately the same time are associated with the ions' entry into the drift chamber. It is to be appreciated that a variety of data, including timing data can be combined and analyzed to aid in detection and/or identification of material from the sample. For example, data from a run in which the ion modifier was not functioning is correlated with data from a run in which the ion modifier operated. Thus, data associated with the operation of the ion modifier can be used to differentiate or confirm the identity of ions that have similar ion mobiles.

In embodiments, the IMS 100, including its components, operates under computer control. For example, a processor included with or in the IMS to control the IMS's components and functions described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the IMS 100. In the case of a software implementation, the module, functionality, or logic represents program code that performs specified tasks when executed on a processor (e.g., CPU or CPUs). The program code may be stored in one or more computer-readable memory devices (e.g., memory and/or one or more tangible media), and so on. The structures, functions, approaches, and techniques described in this document can be implemented on a variety of commercial computing platforms having a variety of processors.

Processors are not limited by the materials from which they are formed or the processing mechanisms employed therein. For example, the processor may be comprised of semiconductor(s) and/or transistors (e.g., electronic integrated circuits (ICs)).

Memory can be included with the processor. The memory can store data, such as a program of instructions for operating the IMS (including its components), data, and so on. Although a single memory device can be used, a wide variety of types and combinations of memory (e.g., tangible memory, non-transitory) may be employed, such as random access memory (RAM), hard disk memory, removable medium memory, external memory, and other types of computer-readable storage media.

In additional embodiments, a variety of analytical devices may make use of the structures, techniques, approaches, and so on described herein. Thus, although an IMS device is described throughout this document, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Moreover, the processor controlling the IMS 100 may be configured to communicate with a variety of different networks. For example, the networks may include the Internet, a cellular telephone network, a local area network (LAN), a wide area network (WAN), a wireless network, a public telephone network, an intranet, and so on.

Having discussed various configurations, operations of spectrometers in accordance with the present disclosure in conjunction with FIG. 1, additional configurations/operational aspects of spectrometers including ion modifiers are now discussed. It is to be appreciated that the components, configurations, approaches, techniques, operating parameters can be used in conjunction with the aspects discussed with respect to FIG. 1 and FIG. 4.

FIGS. 2A-D illustrate an IMS 200 in an example implementation in which an modifier 226 is used to modify a portion of the ions that are admitted to a drift chamber 106.

Figure 2A:
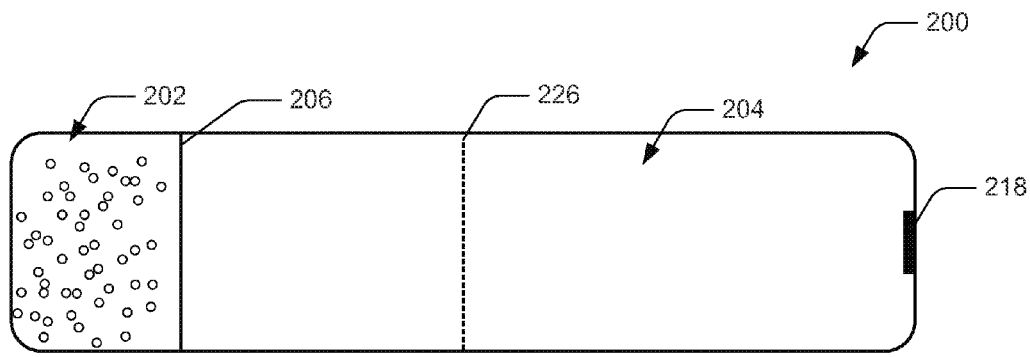
FIGS. 2A-D are diagrammatic illustrations of spectrometers in accordance with the present disclosure.

FIG. 2A is an illustration of the IMS 200 in a configuration in which an ionization source ionizes material such as molecules, atoms, from a sample of interest in the ionization chamber. As illustrated, the gate 206 is closed to keep the ions in the ionization chamber. The gate may be closed by placing a repelling charge on the gate to prevent ions from entering the drift chamber 206. The gate can, for instance, force ions with a larger charge further away from the gate in comparison to ions with a lower charge.

Figure 2B:
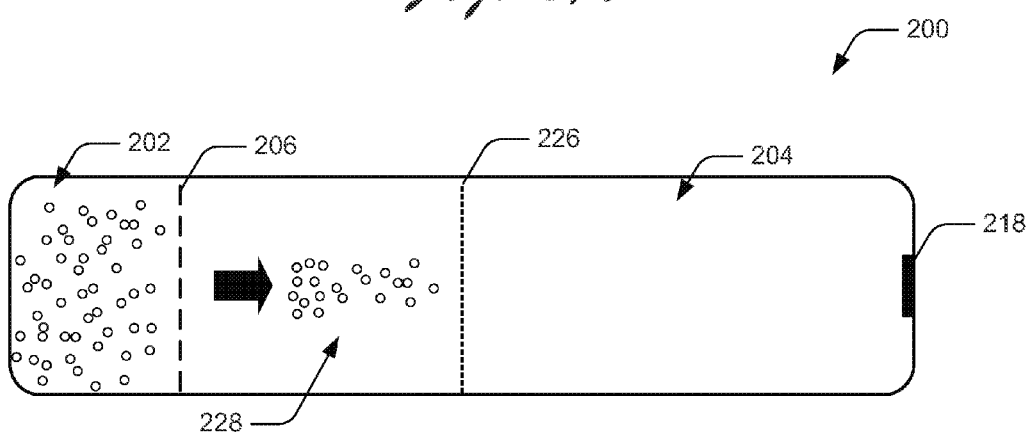

FIG. 2B illustrates a IMS 200 in a configuration so at least some of the ions enter the drift chamber 204. The ions 228 can be drawn toward a detector 218 under the influence a field generated by the focusing rings, responsive to removal of a repelling charge on the gate 206. Individual ions can enter the drift chamber 204 based on their ion mobility. For example, ions adjacent the gate, prior to a repelling charge being dropped, enter the drift chamber before ions that were forced away from gate. The ions 228 in the drift chamber can separate as they travel toward the ion modifier 226. For example, the ion modifier 226 is positioned approximately at the drift chamber's midpoint so the ion modifier can selectively modify a portion of the ions that entered the drift chamber 204.

Figure 2C:
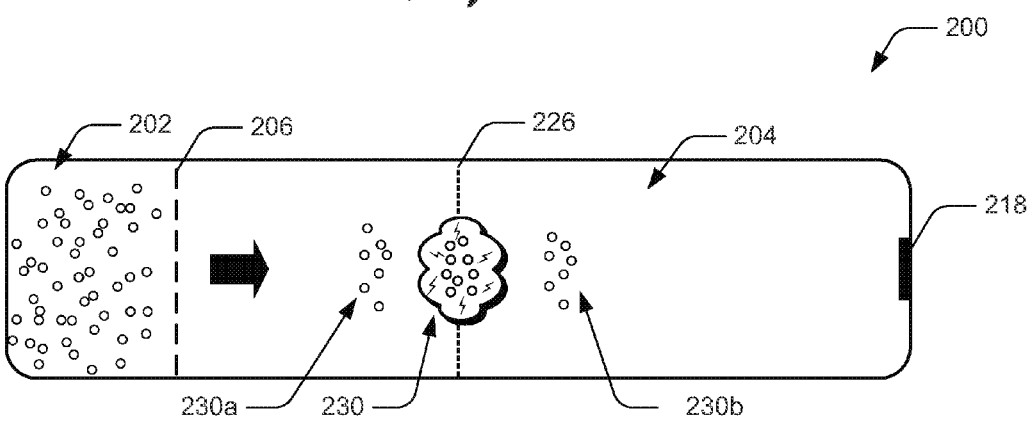

FIG. 2C illustrates the IMS 200 in a configuration in which the ion modifier modifies a portion of the ions 230. As illustrated, the ion modifier can modify selected ions based on the time it takes the ions to reach the ion modifier 226. For example, a computing system controlling operation of the gate and or the ion modifier 226 can time opening of the gate, operation of the ion modifier and/or with detector response in order to identify material from the sample of interest. For instance, the ion modifier 226 can modify ions associated with intermediate speed 5 milliseconds (ms) (230) while neutralizing or not modifying ions traveling faster, e.g., 2 ms (230*b*), or slower, e.g., 7 ms (230*a*). In embodiments, the computing system can time how long it takes an ion to travel from the gate to the detector. The computing system can time the interval between opening the gate and operation of the ion modifier, e.g., dictate the time between opening of the gate and operation of the modifier.

The computing system can associate this time with the time it takes ions, fragments and so forth (that result from modifying a selected portion of the ions) to reach the detector. In embodiments, data, including but not limited to, time-of-flights between different runs are associated with one another to identify the material from the sample of interest. It is to be appreciated that the IMS 200 can change other operating configurations in addition to operation of the ion modifier, e.g., the IMS uses dopant in a subsequent run based on ambiguous identification in a previous run.

In embodiments, the ion modifier can neutralize ions that are not selected. For example, the controller is configured to cause the ion modifier to neutralize at least some of the other ions. The ion modifier can cause ions that are not selected to be attracted to the electrodes included in the ion modifier and/or the focusing rings where the ions are neutralized. In an initial run, for example, an IMS can produce peaks at two milliseconds, five milliseconds and seven milliseconds, while in a second run the ion modifier can be configured to eliminate the ions associated with the two and seven millisecond peaks so ions or fragments of ion passing to the detector are only associated with ions from the five millisecond peak.

Figure 2D:
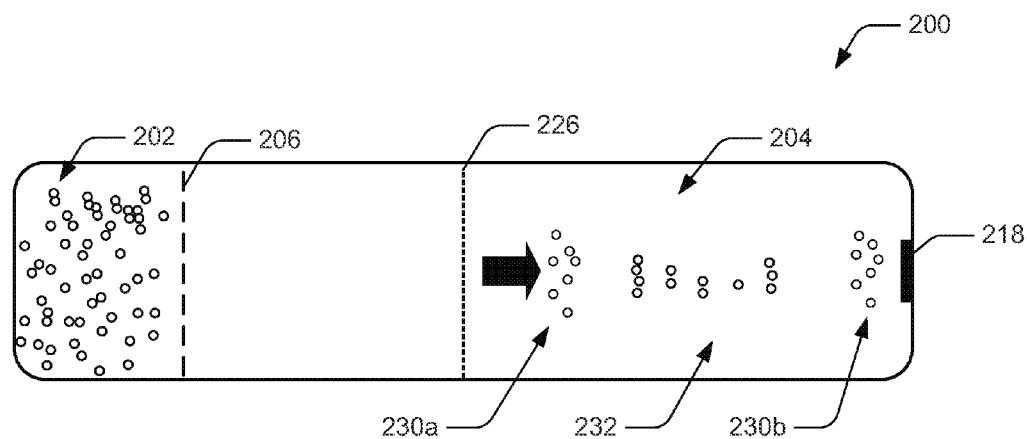
Figure 3A:
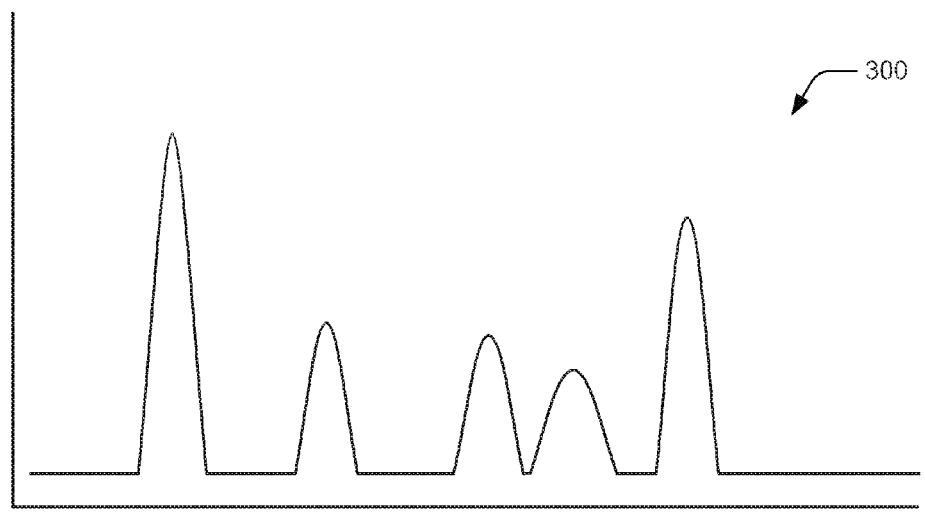
FIGS. 3A-C are illustrations of plasmagrams that indicate example operation of an ion modifier in accordance with the present disclosure.
Figure 3B:
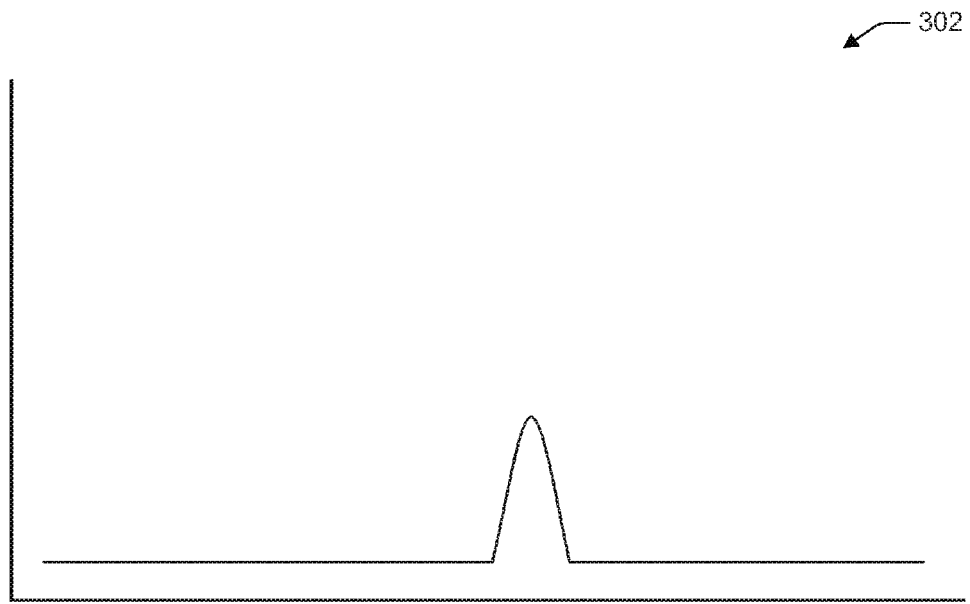
Figure 3C:
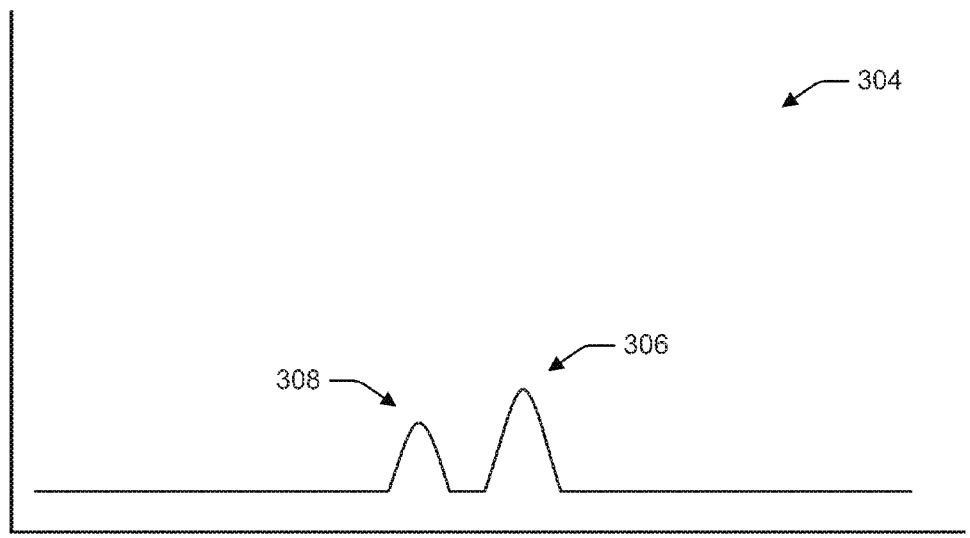

FIG. 2D illustrates a IMS 200 in a configuration in which ions and/or fragments of ions 232 that were modified separate as they pass towards the detector 218. The ions can separate based on the ions', respective, ion mobility. FIGS. 3A-C are illustrations of plasmagrams to show operation of ion modifiers in accordance with the present disclosure. These plasmagrams are included for illustrative purposes only.

FIG. 3A illustrates a plasmagram 300 in which the ion modifier is not functioning. This plasmagram represents a sample detector output during an initial run in which the ion modifier is not used. Multiple peaks may be present due to detection of ions having different ion mobilities. One or more of the peaks can be ambiguously identified, such as not identified, due to a variety of reasons, such as low concentration in the sample of interest, and so on.

FIG. 3B is an illustration of a plasmagram 302 showing a single peak, from the initial run, in which the ion modifier is to modify corresponding ions in a subsequent run. The peak may be selected manually or automatically by a computing system controlling ion modifier and/or detector. For example, the computing system may select the peak to further confirm the identity of the ions associated with the peak or to differentiate between ions of interest (e.g. a drug, toxic chemical) and a contaminate with a similar ion mobility. While an IMS with an ion modifier can be operated to isolate a single peak, in embodiments, the plasmagram of FIG. 3B may be a computer manipulation of the plasmagram illustrated in 3A.

FIG. 3C is an illustration of a plasmagram 304 illustrating operation of an ion modifier in accordance with the present disclosure. The ion modifier, for example, can be used to neutralize ions associated with the peaks of FIG. 3A that are not of interest and to modify ions that correlate to the peak of interest in FIG. 3B. The plasmagram in FIG. 3C illustrates that two peaks, respectively, a peak with a charge on a molecule 306 and a fragment peak 308 that results from modifying a portion of the ions using RF.

Having described systems, components, techniques, modules and approaches that can be implemented, in accordance with the present disclosure, sample procedures are now described that can be implemented with the systems, components, techniques, modules and approaches above.

Example Procedures

The following discussion describes procedures that may be implemented utilizing the previously described IMS 100 components, techniques, approaches, and modules. Aspects of each of the procedures may be implemented in hardware, software, or a combination thereof. The procedures are shown as a set of blocks that specify operations performed by one or more devices (e.g., a spectrometer, a computer system controlling a spectrometer or spectrometer components) and are not necessarily limited to the order shown for performing the operations by the respective blocks. In portions of the following discussion, reference will be made to the IMS 100 of FIG. 1.

Figure 4:
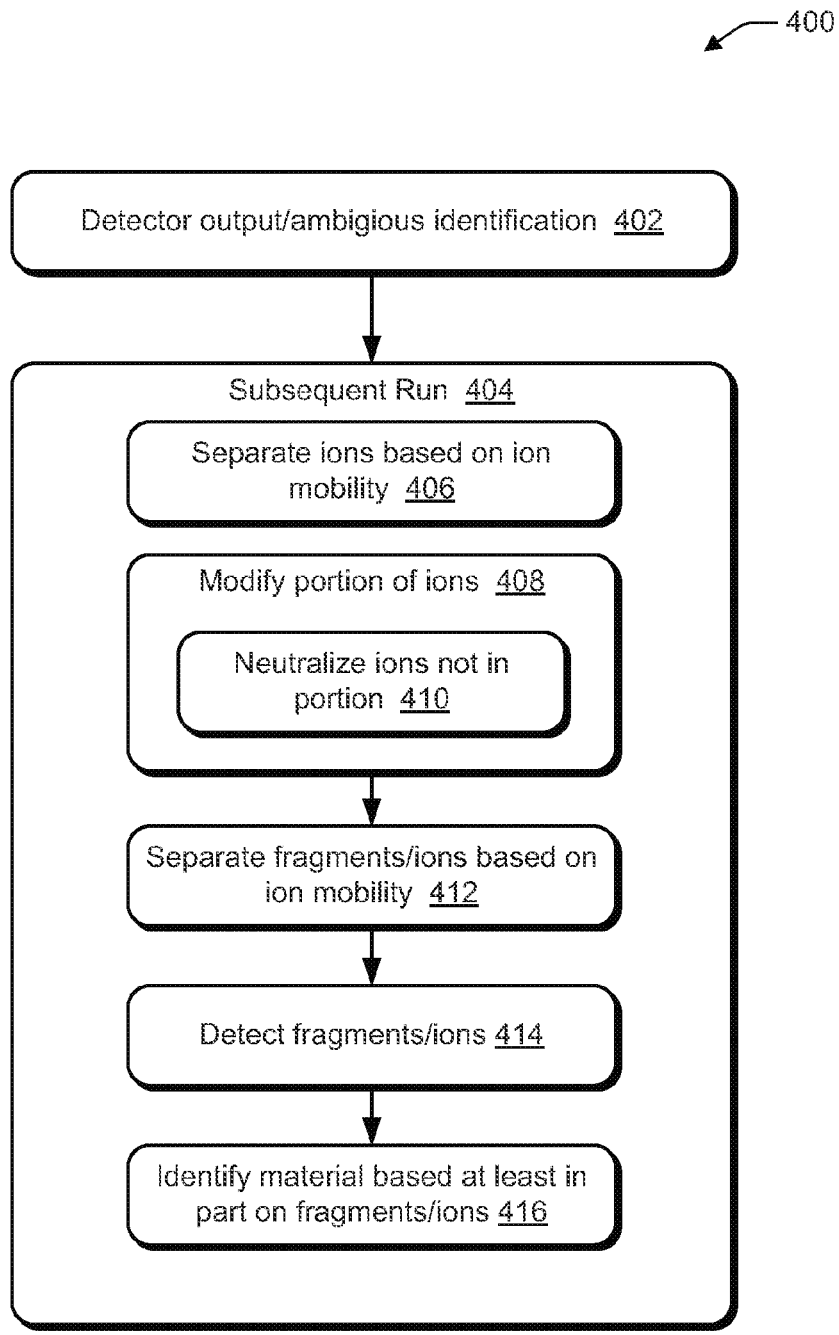
FIG. 4 is a flow diagram depicting a detection procedure that implements separation of ions to be modified.

FIG. 4 depicts a procedure 400 in an example implementation in which ions are modified to aid detection and/or identification of material from a sample of interest. For example, an ion modifier is used to modify selected ions to increase identification accuracy in comparison to not modifying at least some of the ions. In embodiments, the procedure 400 is performed under computer control.

Optionally, an initial run is performed in which detector response is ambiguous with regard to identification of the material from the sample of interest (block 402). For example, a peak in an initial run may be obscured, difficult to detect, or not detected for a variety of reasons. The initial run can be performed without modifying a portion of the ions to minimize overall power consumption, and so forth.

In embodiments, responsive to ambiguous identification, a subsequent run is performed (block 404). For example, when a computing system controlling operation of an IMS fails to identify material from a sample of interest, it can trigger a subsequent run in which some of the ions are modified. For example, in response to non-detection, the ion modifier 126 fragments at least some of the ions that correspond to ions associated with a particular peak in the (previous) initial run.

Ions, formed from a sample of interest, are allowed to separate based on their respective ion mobilities (block 406). For example, at least some ions from a sample of interest enter the drift chamber 106 responsive to when the potential on the moving grid is made to be substantially equal to that on the fixed grid. In embodiments, the ions separate based on their ion mobility as they pass for detection.

A portion of the ions are modified (block 408). Modifying can include applying a radio frequency (RF) to a portion of the ions to fragment them so the resulting fragments that are ionized can be detected and/or identified. Modifying can include neutralizing the ions, e.g., preventing ion and/or the fragments from passing for detection by neutralizing them. For example, passage of ions corresponding to the portion is temporarily stopped, e.g. by destruction of the ions, before an RF is applied to modify the ions and, subsequently, release the ions and/or resulting fragments to pass for detection. Optionally, modifying can include neutralizing ions that are not of interest. For example, an IMS including an ion modifier performing the method can modify ions that take 5 ms to pass through the drift chamber while preventing ions from being detected that take 2 ms or 7 ms to pass from the gate to the detector. The ions can be neutralized such as contacting the ion modifier and/or another electrode.

Ions that result from modifying the ions in the portion, separate based on their respective ion mobility (block 410). For example, fragments that result from modifying the ions can have a shorter time-of-flight than an ion of a molecule. The fragments and ions can separate based on their, respective, ion mobilities as they travel from the ion modifier to the detector. A spectrometer performing the procedure can time one or more of the time from opening the gate to modifying or the time it takes the fragments and/or ions from being modified to reach the detector.

The fragments and/or ions that result from modifying the ions are detected (block 412). For example, the detector can generate an output that is used to identify the material from the sample of interest. A computing system performing the method can identify the material, e.g., molecules from the sample of interest, at least in part based on the fragments and/or ions resulting from modifying the ions within the portion.

This application incorporates by reference in its entirety Great Britain (GB) Patent Application Number 1101132.7, entitled Combined Ion Gate and Ion Modifier, filed on 21 Jan. 2011.

Although the invention has been described in language specific to structural features and/or methodological acts, it is to be understood that the invention defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claimed invention.

What is claimed is:

1. A spectrometer comprising:
an ion modifier disposed in a drift chamber that has a gate that is configured to control entry of ions to the drift chamber, the ion modifier being configured to modify a portion of the ions that enter the drift chamber; and
a controller, communicatively coupled to the ion modifier, to control operation of the ion modifier to select a portion of ions formed from a sample, and to prevent other ions from passing toward a detector, wherein the controller is configured to synchronize operation of the ion modifier with opening of the gate to select the portion of ions to be modified,
wherein the controller is configured to control operation of the ion modifier to select the portion of the ions based on a previous response of the detector.

2. The spectrometer of claim 1, wherein the ion modifier is further configured to neutralize at least some of the other ions.

3. The spectrometer of claim 1, wherein the controller is further configured to cause the ion modifier to modify at least some of said ions in the portion responsive to ambiguous identification, during previous operation of the spectrometer, of the other ions that correspond to said ions in the portion.

4. The spectrometer of claim 1, wherein the ion modifier is configured to fragment of at least some of said ion in the portion.

5. The spectrometer of claim 1, wherein the spectrometer is configured to operate substantially at ambient pressure.

6. The spectrometer of claim 1, wherein the spectrometer is configured to time arrival of at least some fragments formed by modifying said ions in the portion with operation of the gate and the ion modifier.

7. The spectrometer of claim 1, wherein the spectrometer is configured to time arrival of at least some fragments formed by modifying said ions in the portion with operation of the ion modifier.

8. The spectrometer of claim 1, wherein the ion modifier is configured to modify at least some of said ions in the portion with a radio frequency.

9. The spectrometer of claim 1, wherein the gate and the ion modifier are spaced apart from one another to permit separation of the ions admitted to the drift chamber.

10. The spectrometer of claim 1, wherein the controller is further configured to synchronize operation of the ion modifier with opening of the gate to select the portion of ions to be modified.

11. An ion mobility spectrometer comprising:
a gate configured to control entry of ions to a drift chamber, the gate disposed on an end of the drift chamber generally opposite a detector;
an ion modifier disposed between the gate and the detector so the ions, respectively, separate between the gate and the ion modifier based on the ions' ion mobility; and
a controller, coupled to the ion modifier, the controller configured to synchronize operation of the ion modifier so fragments that result from operation of the ion modifier are associated with a portion of the ions based on ion mobility, and wherein the controller is further configured to time operation of the ion modifier to prevent ions that are not in the portion from passing to the detector,
wherein the controller is configured to control operation of the ion modifier to select the portion of the ions based on a previous response of the detector.

12. The ion mobility spectrometer of claim 11, wherein the ion modifier is further configured to prevent a substantial portion of the other ions from passing to the detector.

13. The ion mobility spectrometer of claim 11, wherein the ion modifier is further configured to neutralize substantially all the other ions.

14. The ion mobility spectrometer of claim 11, wherein the ion modifier is further configured to neutralize at least some of the other ions.

15. The ion mobility spectrometer of claim 11, wherein the controller is further configured to cause the ion modifier to operate responsive to a determination that other ions corresponding to the portion were not identified by the detector during previous operation.

16. The ion mobility spectrometer of claim 11, wherein the ion mobility spectrometer is further configured to time detection of at least some of the fragments with operation of the gate and the ion modifier.

17. A method comprising:
separating ions in a drift chamber based on ion mobility;
fragmenting a portion of the ions, said ions in the portion having substantially similar ion mobilities; and
separating fragments that are ionized, respectively, based on said fragment's ion mobility; and
synchronizing operation of a gate and an ion modifier to prevent at least some other ions that are not in the portion from passing toward the detector,
wherein the method is performed responsive to non-identification of other ions corresponding to the portion during previous operation of a spectrometer.

18. The method of claim 17, further comprising neutralizing at least some other ions.

19. One or more computer-readable media comprising instructions, that responsive to being executed by a computing system, cause the computing system to:
cause an ion modifier, disposed in a drift chamber between a gate and a detector, to modify ions that correspond to other ions that were ambiguously identified during previous operation of the detector;
identify molecules included in a sample of interest based on ion mobilities associated with fragments that result from the ion modifier modifying the ions formed from the molecules; and
synchronize operation of the gate and the ion modifier to select a portion of the ions to be modified,
wherein the method is performed responsive to non-identification of other ions corresponding to the portion during previous operation of a device.

20. One or more computer-readable media of claim 19, wherein the instructions are further executable to base identification at least in part on a time between operation of the ion modifier and detection of the fragments.

21. One or more computer-readable media of claim 19, wherein said identification is at least partially based on the detector's response during previous operation of the detector.

22. One or more computer-readable media of claim 19, wherein the instructions are further executable to cause the ion modifier to neutralize at least some of the other ions.

23. The spectrometer of claim 1 wherein the ion modifier comprises at least two electrodes that are spaced apart from one another along a length of the drift chamber.

24. The spectrometer of claim 23 wherein the at least two electrodes comprise at least one of:
(i) sets of parallel wires, or
(ii) wire mesh.

25. The spectrometer of claim 23 wherein the controller is configured to apply a direct current (DC) field between the at least two electrodes and in a direction of the length of the drift chamber to neutralise the at least some other ions that are not in the portion of ions to be modified to prevent them from passing toward the detector.

26. The ion mobility spectrometer of claim 11 wherein the ion modifier comprises at least two electrodes that are spaced apart from one another along a length of the drift chamber.

27. The ion mobility spectrometer of claim 23 wherein the at least two electrodes comprise at least one of:
(i) sets of parallel wires, or
(ii) wire mesh.

28. The spectrometer of claim 23 wherein the controller is configured to apply a direct current (DC) field between the at least two electrodes and in the direction of the length of the drift chamber length to neutralise the at least some other ions that are not in the portion to prevent them from passing toward the detector.

29. The method of claim 17 wherein preventing at least some other ions that are not in the portion from passing toward the detector comprises applying, between at least two electrodes of the ion modifier, a direct current (DC) field in the direction of a length of the drift chamber to neutralise the at least some other ions.

* * * * *